US009005294B2

(12) United States Patent
You et al.

(10) Patent No.: US 9,005,294 B2
(45) Date of Patent: Apr. 14, 2015

(54) ARTIFICIAL DISK FOR TRANSFORAMINAL LUMBAR INTERBODY FUSION (TLIF) AND INSERTION ASSEMBLY THEREOF

(75) Inventors: Chang-Hwa You, Gunpo-si (KR); Boo-Gyu Park, Incheon (KR); Yun-Sung Kang, Gunpo-si (KR); Ju Yun, Bucheon-si (KR); Dong-min Kim, Gunpo-si (KR)

(73) Assignee: BM Korea Co., Ltd., Gunpo-Si, Gyeonggi-Do (KR)

( * ) Notice: Subject to any disclaimer, the term of this patent is extended or adjusted under 35 U.S.C. 154(b) by 187 days.

(21) Appl. No.: 13/464,246

(22) Filed: May 4, 2012

(65) Prior Publication Data
US 2013/0268077 A1    Oct. 10, 2013

(30) Foreign Application Priority Data
Apr. 9, 2012    (KR) .................. 10-2012-0036721

(51) Int. Cl.
*A61F 2/44*    (2006.01)
*A61F 2/46*    (2006.01)
*A61F 2/28*    (2006.01)
*A61F 2/30*    (2006.01)

(52) U.S. Cl.
CPC .............. *A61F 2/4455* (2013.01); *A61F 2/4465* (2013.01); *A61F 2/4611* (2013.01); *A61F 2002/2835* (2013.01); *A61F 2002/30365* (2013.01); *A61F 2002/30481* (2013.01); *A61F 2002/30492* (2013.01); *A61F 2002/30518* (2013.01); *A61F 2002/30538* (2013.01); *A61F 2002/30779* (2013.01); *A61F 2002/30784* (2013.01); *A61F 2002/30785* (2013.01); *A61F 2002/30822* (2013.01); *A61F 2002/30843* (2013.01); *A61F 2002/4629* (2013.01)

(58) Field of Classification Search
CPC .......... A61F 2/44; A61F 2/4611; A61B 17/88
USPC .......................... 606/86 A; 623/17.11–17.16
See application file for complete search history.

(56) References Cited

U.S. PATENT DOCUMENTS

| 2006/0229627 A1* | 10/2006 | Hunt et al. ...................... 606/86 |
| 2007/0225726 A1* | 9/2007 | Dye et al. ......................... 606/99 |
| 2008/0221694 A1* | 9/2008 | Warnick et al. ............. 623/17.16 |
| 2012/0123548 A1* | 5/2012 | Lynn et al. .................. 623/17.16 |

\* cited by examiner

*Primary Examiner* — Christopher Beccia
(74) *Attorney, Agent, or Firm* — John K. Park; Park Law Firm (57) ABSTRACT

An assembly for inserting an artificial disk is provided. The assembly includes an artificial disk, which includes a body which has a predetermined thickness to be inserted between vertebrae, and includes an incision recess incised on one side of the body in a sideways direction and a penetrating hole formed on the side on which the incision recess is formed in a vertical thickness direction, and a connecting unit which is inserted into the penetrating hole and serves as a shaft of a rotational movement of the body, and includes a connecting hole formed on a side surface of the connecting unit, and a guide protrusion, a first insertion tool which includes a connecting rod, and a handle, and a second insertion tool which includes a support rod, an insertion end, a support end, and a handle.

7 Claims, 7 Drawing Sheets

Conventional Art

ARTIFICIAL DISK FOR TRANSFORAMINAL LUMBAR INTERBODY FUSION (TLIF) AND INSERTION ASSEMBLY THEREOF

PRIORITY

This application claims the benefit under 35 U.S.C. §119 (a) of a Korean patent application filed on Apr. 9, 2012 in the Korean Intellectual Property Office and assigned Serial No. 10-2012-0036721, the entire disclosure of which is hereby incorporated by reference.

BACKGROUND OF THE INVENTION

1. Field of the Invention

The present invention relates to an artificial disk and an insertion assembly thereof. More particularly, the present invention relates to an artificial disk which is used in a spinal fusion procedure for a spinal disease patient, and surgical instruments to insert the artificial disk easily.

2. Description of the Related Art

In general, an intervertebral disk absorbs weight and shock of a body between vertebrae except for some of the cervical spine, and serves as a buffer to disperse shock like a spring. The intervertebral disk holds the vertebrae so that the vertebrae are not dislocated, separates two vertebrae so that the spinal nerves are not pressed, broadens a range of a spinal joint pore, and allows smooth movement of each vertebra.

Such an intervertebral disk of a human being generally consists of annulus fibrosus and nucleus pulposus. The annulus fibrosus controls movement of spinal segments and 70~80% of the inner nucleus pulposus is moisture. The intervertebral disk buffers or transmits weight or shock vertically applied. However, in a degenerative disk disease, the annulus fibrosus becomes weak in its movement and capability of containing the nucleus pulposus, and a moisture content is reduced. Accordingly, this complex result causes diseases such as spinal stenosis, osteophyte formation, disk herniation, and nerve root pressure.

One of the methods for curing diseases caused by the intervertebral disk is removing a damaged intervertebral disk from a body and replacing the disk with an artificial disk (a so-called cage) in a space between two adjacent vertebral bodies. That is, this method is to make the spine as natural as possible by implanting an artificial disk and restore an original function to the spine by restoring an original distance between two adjacent vertebral bodies, which corresponds to an original height of the intervertebral disk.

The artificial disk has an appropriate thickness and an anatomic type so that the original height of the intervertebral disk is restored, and has a hole to facilitate growth of bones afterward and a mounting part to be mounted on an insertion tool.

The transforaminal lumbar interbody fusion (TLIF), which is one of the surgical methods of inserting an artificial disk between vertebrae, is one of the spinal fusion methods, and is a surgical technique to access a disk from a posterior portion and insert an intervertebral artificial disk. That is, the TLIF is a surgical procedure in which a small incision is made along both sides of a vertebral muscle and the spine is exposed to the minimum so that a screw nail is fixed, and a spinal joint portion is removed in a direction in which a neuropore comes out and an artificial disk is inserted. The TLIF is primarily used in recent years because of less bleeding and a reduced surgery time.

Figure 7:
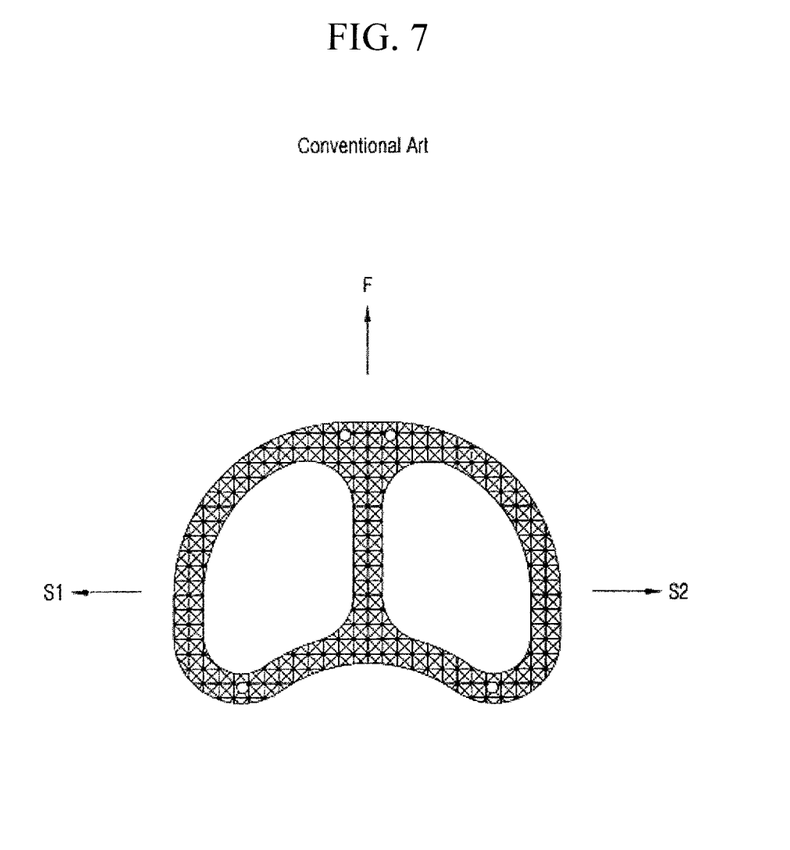
FIG. 7 is a view of a related-art cage according to the related art.

In this method, in order to make a minimum incision and minimize interference in the body, one side surface S1 of a cage is inserted through a posterior portion (a back) of a body first, as shown in FIG. 7, and is placed between vertebrae, and then, a front surface F of the cage is oriented to a front side of the vertebrae (a belly of the body).

That is, an impactor which is to orient the front surface F of the inserted cage to the front side of the vertebrae, is required. The cage is placed in an appropriate position by applying a force to the opposite side surface S2 of the cage using the impactor and then rotating the cage. However, the impactor makes the surgical procedure more difficult and is controlled only by a surgeon.

A method for facilitating placement of such a cage is disclosed in Korean Patent Publication No. 10-2008-0113029. This related art has a connector of a spatula type which is curved to insert a cage which is curved to correspond to vertebrae, and a tube which is bent by a predetermined angle. Such a related art configuration is to insert the cage from a posterior portion (a back of a body) and place the cage to be oriented to a front side (a belly of a body) of the vertebrae. The aim of the TLIF is to achieve this procedure.

However, there is a problem in that the cage should be inserted in a curved form and thus an incision width becomes larger. Therefore, it is difficult to insert the cage because of the shape problem.

Also, the tube is bendable to some extent in order to place the cage to be oriented to the front side of the vertebrae, but a bendable width is not large. Even if the width is larger, the tube puts a limit to exactly placing the cage to be oriented to the front side of the vertebrae.

Therefore, the procedure greatly depends on surgeon's experience, and the impactor, which is an aid to set the location of the inserted cage exactly, is still required.

SUMMARY OF THE INVENTION

Aspects of the present invention are to address at least the above-mentioned problems and/or disadvantages and to provide at least the advantages described below. Accordingly, an aspect of the present invention is to provide an artificial disk which can be easily seated in an exact position between vertebrae without assistance of other aids, and an assembly including an insertion tool thereof.

In accordance with an aspect of the present invention, an assembly for inserting an artificial disk is provided. The assembly includes an artificial disk which includes, a body which has a predetermined thickness to be inserted between vertebrae, and includes an incision recess incised on one side of the body in a sideways direction and a penetrating hole formed on the side on which the incision recess is formed in a vertical thickness direction, and a connecting unit which is inserted into the penetrating hole and serves as a shaft of a rotational movement of the body, and includes a connecting hole formed on a side surface of the connecting unit, and a guide protrusion to be inserted into a guide recess formed on a part of the body that is not incised, a first insertion tool which includes a connecting rod which has a predetermined length and has a connecting protrusion formed on one end thereof in a stepwise shape to be inserted into the connecting hole, and a handle which is formed on the other end, and a second insertion tool which includes a support rod which has a predetermined length and has a hollow through which the connecting rod of the first insertion tool penetrates, and which includes an insertion end which is formed on one end of the support rod to be inserted into the incision recess and is rounded in a shape corresponding to an appearance of the connecting unit, and a support end which projects from the insertion end in a stepwise shape and is rounded in a shape corresponding to an appearance of the side of the body on which the incision recess is formed, and a handle which is formed on the other end.

The support end of the support rod may be rounded in the shape corresponding to the appearance of the side of the body on which the incision recess is formed, so that a rotational movement of the body is limited to a maximum rotation radius between opposite ends of the incision recess formed along an outer circumference of the body, and the incision recess may have an incision length of one side longer than that of the other side with reference to a lengthwise direction of the connecting rod.

The incision length of the one side of the incision recess may limit the rotational movement of the body within 90°.

The rotational movement of the body, which is rotated about the connecting unit, may be limited by the guide protrusion of the connecting unit corresponding to the guide recess.

A length of the guide recess may limit the rotational movement of the body within 90°.

The artificial disk may further include a first fixing part which covers one side of the penetrating hole and has a diameter larger than that of the penetrating hole, and which is inserted into an uneven portion formed on the body and has a shaft rod to be inserted into a shaft hole formed in the connecting unit, and a second fixing part which covers the other side of the penetrating hole and has a diameter larger than that of the penetrating hole, and which is inserted into an uneven portion formed on the body and has a shaft rod connecting hole into which the shaft rod of the first fixing part is inserted.

If the connecting protrusion of the first insertion tool is tightly screwed into the connecting hole of the connecting unit, the connecting unit may be brought into close contact with the insertion end and the support end of the second insertion tool and the body may be brought into close contact with the support end, so that the body is not rotated unless an external force greater than a predetermined force is applied.

According to another aspect of the present invention, an artificial disk including a body which has a predetermined thickness to be inserted between vertebrae is provided. The disk includes an incision recess incised on one side of the body in a sideways direction and a penetrating hole formed on the side on which the incision recess is formed in a vertical thickness direction, and a connecting unit which is inserted into the penetrating hole and serves as a shaft of a rotational movement of the body, and includes a connecting hole formed on a side surface of the connecting unit to be connected with an artificial disk insertion tool, and a guide protrusion to be inserted into a guide recess which is formed on a part of the body that is not incised.

The incision recess may have an incision length of one side longer than that of the other side with reference to a lengthwise direction of the body.

The rotational movement of the body, which is rotated about the connecting unit, may be limited by the guide protrusion of the connecting unit corresponding to the guide recess.

A length of the guide recess may limit the rotational movement of the body within 90°.

The artificial disk may further include a first fixing part which covers one side of the penetrating hole and has a diameter larger than that of the penetrating hole, and which is inserted into an uneven portion formed on the body and has a shaft rod to be inserted into a shaft hole formed in the connecting unit, and a second fixing part which covers the other side of the penetrating hole and has a diameter larger than that of the penetrating hole, and which is inserted into an uneven portion formed on the body and has a shaft rod connecting hole into which the shaft rod of the first fixing part is inserted.

According to the present invention, since the rotation of 90° is performed after the artificial disk is inserted between the vertebrae, the artificial disk can be easily inserted in an appropriate position without assistance of aids and a surgical procedure is more effective in comparison with a related-art, and a cost can be saved.

Since the means for controlling the artificial disk to be rotated by 90° or higher is doubly employed, a surgical procedure can be easily performed.

Also, an accident can be prevented during a surgical procedure by preventing the artificial disk from being separated from the insertion tool or preventing an angle from being changed, and the artificial disk can be easily rotated by releasing the screw connection and thus can be easily seated. If the artificial disk needs to be fixed on the way, the artificial disk can be fixed simply by tightening the screw.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWING FIGURES

The above and other aspects, features, and advantages of certain exemplary embodiments of the present invention will be more apparent from the following description taken in conjunction with the accompanying drawings, in which.

Throughout the drawings, it should be noted that like reference numbers are used to depict the same or similar elements, features, and structures.

DETAILED DESCRIPTION OF EXEMPLARY EMBODIMENTS

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used by the description inventor to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
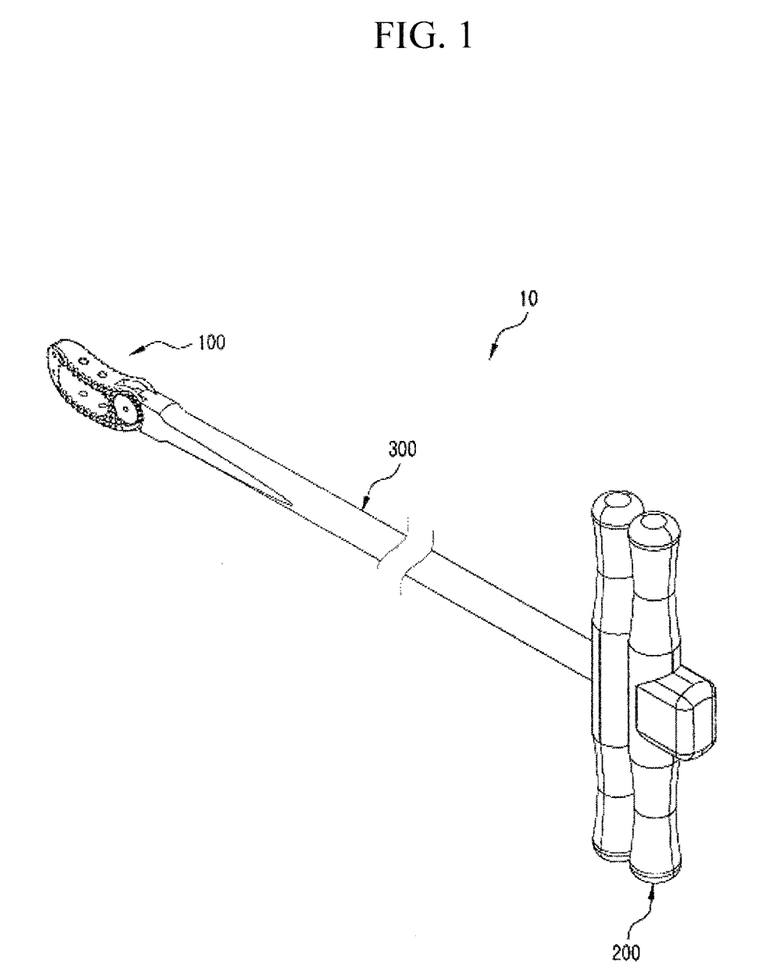
FIG. 1 is a perspective view of an assembly for inserting an artificial disk according to an exemplary embodiment of the present invention.
Figure 2:
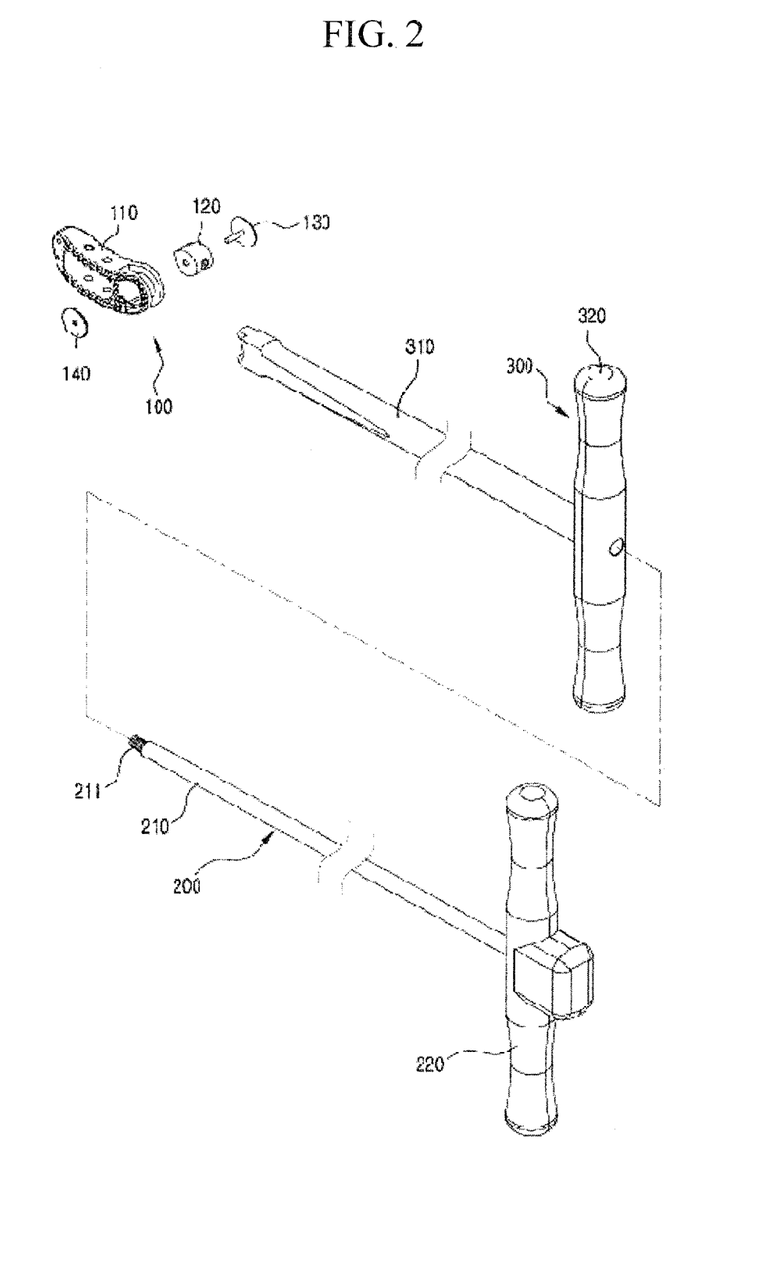
FIG. 2 is an exploded perspective view of the assembly for inserting the artificial disk according to an exemplary embodiment of the present invention.
Figure 3:
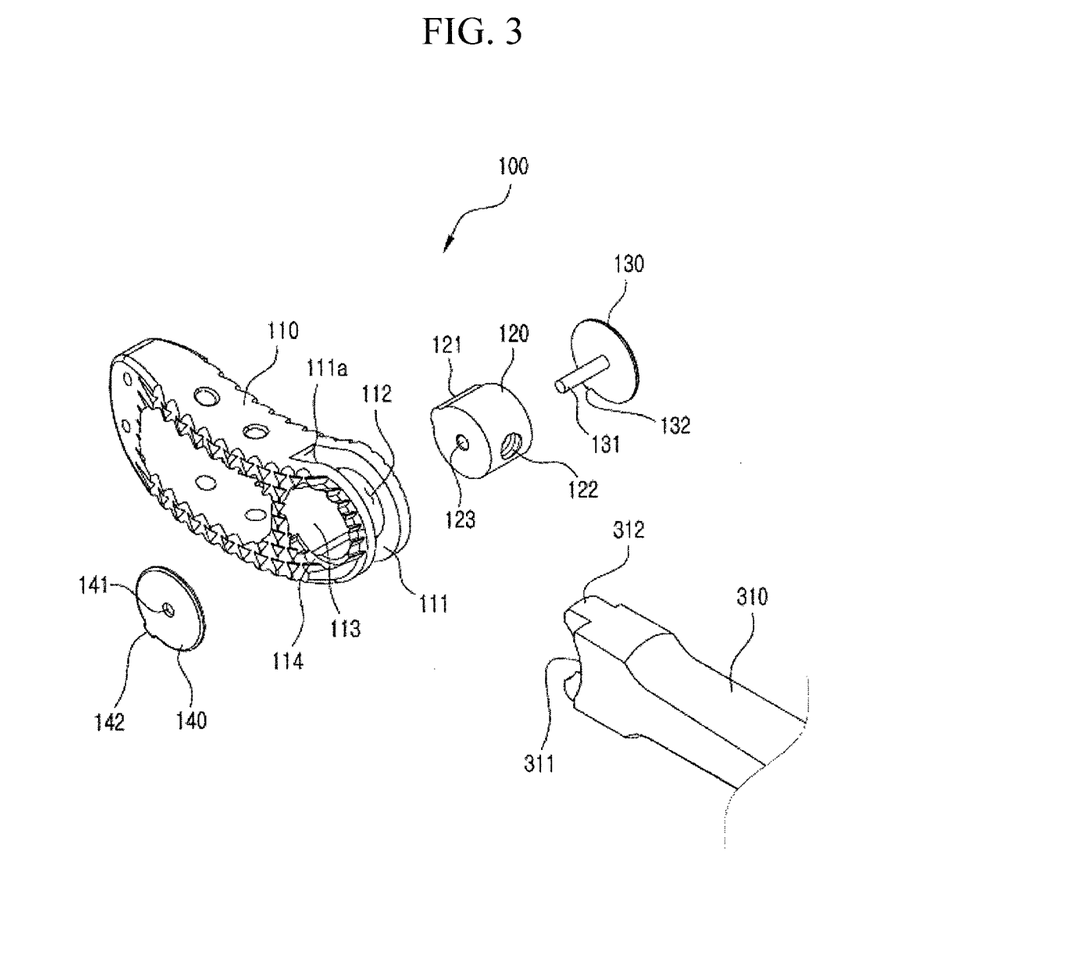
FIG. 3 is an enlarged view of a part of the assembly for inserting the artificial disk according to an exemplary embodiment of the present invention.

FIG. 1 is a perspective view of an assembly for inserting an artificial disk according to an exemplary embodiment of the present invention, FIG. 2 is an exploded perspective view of the assembly for inserting the artificial disk according to an exemplary embodiment of the present invention, and FIG. 3 is an enlarged view of a part of the assembly for inserting the artificial disk according to an exemplary embodiment of the present invention.

Referring to FIGS. 1 to 3, an assembly 10 for inserting an artificial disk according to an exemplary embodiment of the present invention includes an artificial disk 100, a first insertion tool 200, and a second insertion tool 300.

The artificial disk 100 is a prosthetic device that is inserted between vertebrae in replacement of a damaged disk in a TLIF procedure, and the first insertion tool 200 is connected to the artificial disk 100 to be able to insert the artificial disk 100 from a posterior portion of a body and place the artificial disk 100 to be oriented to a front side of the vertebrae. The first insertion tool 200 is inserted into the second insertion tool 300, and is inserted along with the second insertion tool 300 and then is removed from the body along with the second insertion tool 300.

The artificial disk includes a body 110, a connecting unit 120, a first fixing part 130, and a second fixing part 140.

The body 110 has a predetermined thickness to be inserted between the vertebrae, that is, a thickness similar to that of an undamaged disk, and has an anatomically rounded shape to be inserted between the vertebrae appropriately. That is, one side of the body 110 corresponding to a belly after being inserted curves outwards and the other side corresponding to a back curves inwards. That is, the body 110 is rounded in a curved form. The body 110 may have inner holes of different shapes and sizes to facilitate growth of bones.

The artificial disk 100 has an incision recess 111 which is formed on one side of the artificial disk 100, that is, a side to which the insertion tool is connected, and which is incised in a sideways direction S2. An insertion end 312 of a support rod 310 of the second insertion tool 300, which will be described below, is inserted into the incision recess 111. A support end 311 of the support rod 310 is rounded to correspond to an appearance of the side of the body 110 to which the insertion tool is connected, so that the body 110 can determine a rotation radius within an incision range of the incision recess 111 with reference to the support rod 310.

In other words, the incision recess 111 has an incision length of one side longer than that of the other side with reference to a lengthwise direction of the insertion tool. That is, a first incision end 111a is formed longer than a second incision end 111b.

When the artificial disk 100 is connected to the insertion tool, the second incision end 111b is in contact with one side of the insertion end 312 of the second insertion tool 300, and the artificial disk 100 is inserted into the body in a fixed state, so that the body 110 is not rotated beyond a range of the second incision end 111b due to close contact between the second incision end 111b and one side of the insertion end 312. As will be described below, the outwardly curving portion of the body 110 is oriented to the belly F of the body by rotating the body 110 after inserting the artificial disk 100. At this time, the first incision end 111a is in contact with the other side of the insertion end 312, so that a maximum rotation radius is limited and thus the body 110 is not rotated beyond a range of the first incision end 111a.

A penetrating hole 112 is formed in the side of the body 110, on which the incision recess 111 is formed and to which the insertion tool is connected, in a vertical width direction, and the connecting unit 120, which serves as a shaft of the rotation movement of the body 110, is inserted into the penetrating hole 112. A guide recess 113 is formed in the body 110 in a perpendicular direction F to the incision direction of the incision recess 111, and a guide protrusion 121 protruding from the connecting unit 120 is situated within a range of the guide recess 113.

A connecting hole 122 is formed on the connecting unit 120 to form screw connection with a connecting protrusion 211 of the first insertion tool 200, and the connecting unit 120 is formed in a cylindrical shape so that the connecting unit 120 can inserted into the penetrating hole 112 of the body 110, and the guide protrusion 121 of the connecting unit 120 is situated in the guide recess 113 of the body 110, so that the body 110 can be rotated about the fixed connecting unit 120. However, the rotation radius of the body 110 is limited within a range of the guide recess 113 by the guide protrusion 121. The cylindrical connecting unit 120 has a shaft hole 123 into which a shaft rod 131 formed on the first fixing part 130, which will be described later, is inserted.

The first fixing part 130 and the second fixing part 140 cover both sides of the penetrating hole 112, but have a diameter larger than that of the penetrating hole 112 and are inserted into an uneven portion 114 formed on the body 110 around the penetrating hole 112. The shaft rod 131 formed on the first fixing part 130 is inserted into the shaft hole 123 of the connecting unit 120 and then is inserted in a shaft rod connecting hole 141 of the second fixing part 140.

Fixing pieces 132 and 142 are further formed on the first fixing part 130 and the second fixing part 140, respectively, and are connected with recesses of the body 110 and fix the first fixing part 130 and the second fixing part 140 so that the first fixing part 130 and the second fixing part 140 are rotated integrally with the body 110.

As configured above, the body 110 and the first fixing part 130 and the second fixing part 140 connected to the body 110 are rotated about the connecting unit 120 which is connected to the insertion tool.

In order to insert the artificial disk 100 described above between the vertebrae of the body and place the artificial disk 100 in an appropriate position, the first insertion tool 200 and the second insertion toll 300 are configured altogether. The first insertion tool 200 includes a connecting rod 210 of a bar shape having a predetermined length and a handle 220 to manipulate and rotate the artificial disk 100.

The connecting 210 has the connecting protrusion 211 formed on one end thereof in a stepwise protrusion shape, and the connecting protrusion 211 is screwed into the connecting hole 122 of the connecting unit 120 described above.

The second insertion tool 300 includes the support rod 310 of a bar shape having a predetermined length and a handle 320 to manipulate the artificial disk 100. The support rod 310 has a hollow formed therein to allow the connecting rod 210 to enter and leave the hollow.

The support end 311 and the insertion end 312 protruding from the support end 311 in a stepwise shape are formed on one end of the support rod 310. The support end 311 is rounded to correspond to an outer circumference of the body 110 in the sideways direction S2 of the incision recess 111 of the body 110, and the insertion end 312 is rounded to be inserted into the incision recess 111 and to correspond to an outer circumference of the cylindrical connecting unit 120, which is inserted through the penetrating hole 112, so that the artificial disk 100 can be smoothly rotated.

Hereinafter, an operation state of the assembly for inserting the artificial disk according to an exemplary embodiment will be explained with reference to FIGS. 4 to 6.

Figure 4:
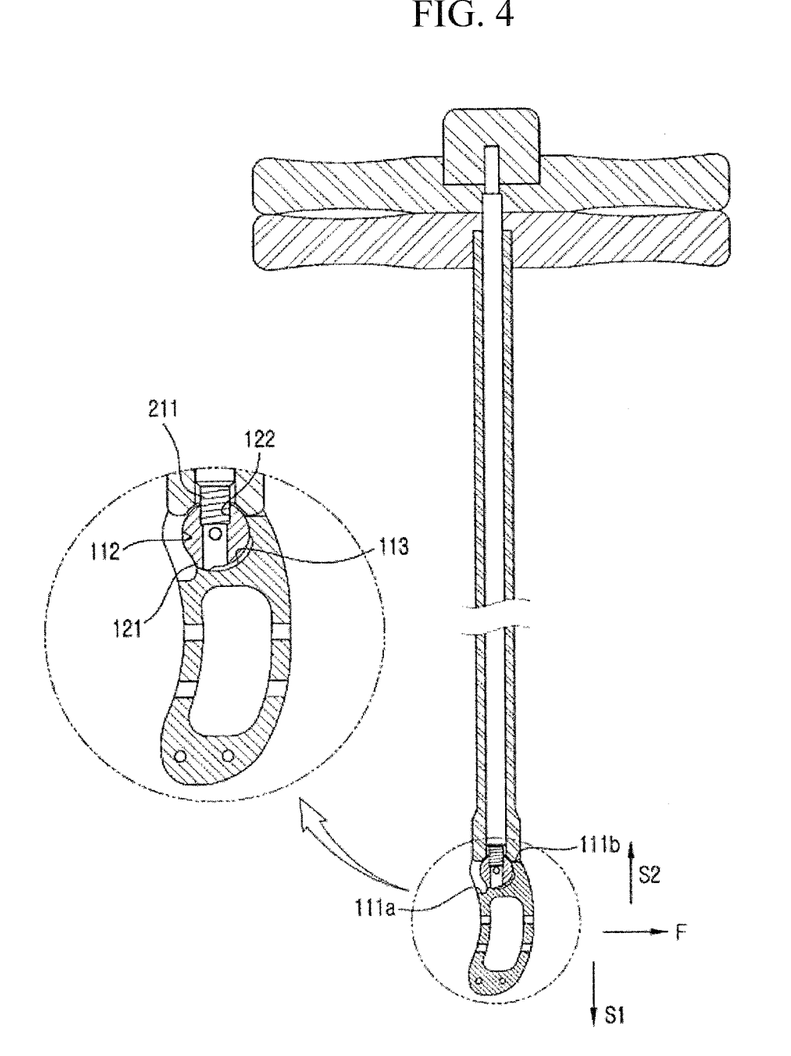
FIGS. 4 to 6 are views illustrating an operation state of the assembly for inserting the artificial disk according to an exemplary embodiment of the present invention.

In FIG. 4, the connecting rod 210 of the first insertion tool 200 is inserted into the support rod 310 of the second insertion tool 300, and, in this state, the connecting protrusion 211 of the connecting rod 210 is screwed into the connecting hole 122 of the connecting unit 120.

Referring to FIG. 4, the insertion end 311 of the support rod 310 is in contact with the second incision end 111b of the incision recess 111 so that the body 110 is not rotated in a direction beyond the range of the second incision end 111b, that is, in an F direction, and, in this state, the artificial disk 100 is inserted toward the vertebrae from a posterior portion of the body.

At this time, the connecting unit 120 is connected in close contact with the first insertion tool 200 to the maximum within the range of the penetrating hole 112 due to the screw connection between the connecting unit 120 and the first insertion tool 200. Therefore, since the connecting unit 120 is connected in close contact with the insertion end 312 and the support end 311 of the second insertion tool 300, the body 100 is not moved unless a considerable external force is applied, and thus the artificial disk 100 is stabilized and is surely inserted into the body.

Figure 5:
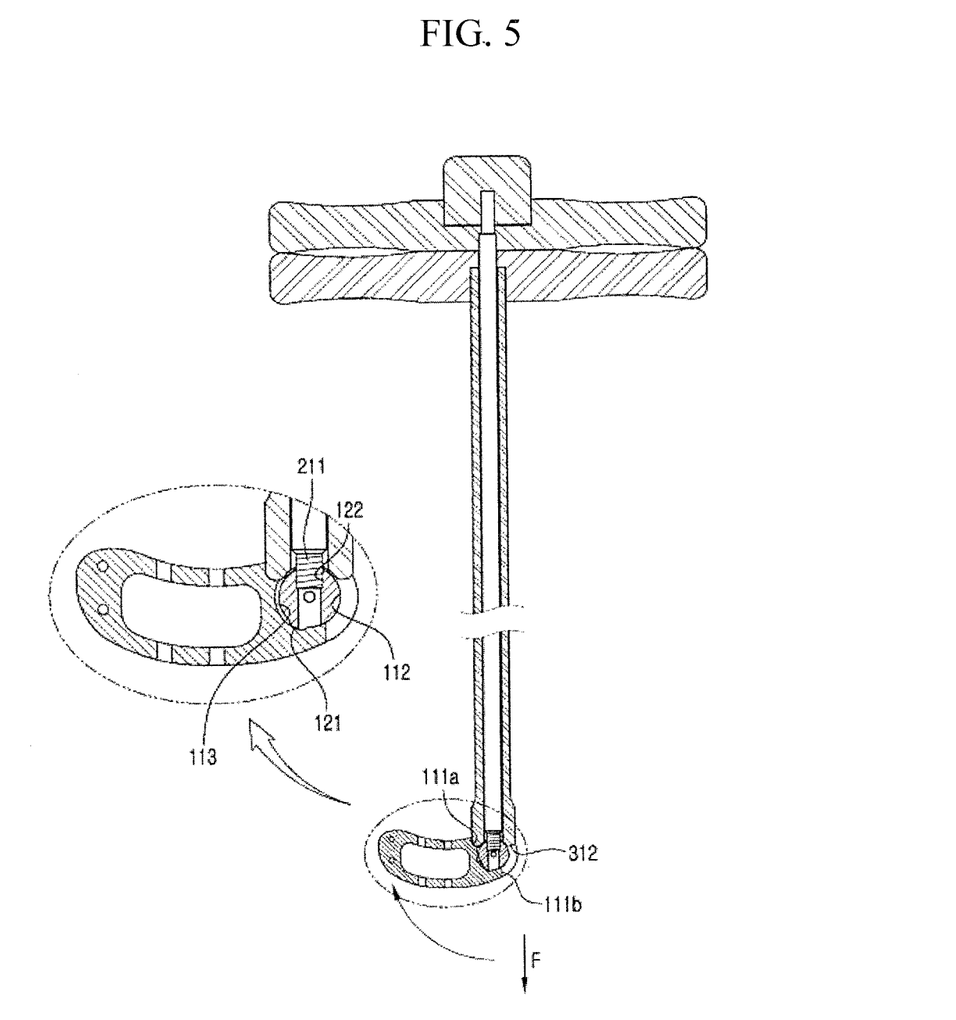

After inserting the artificial disk 100, if the screw connection is slightly released using the handle 220 of the first insertion tool 200, the artificial disk 100 becomes rotatable as shown in FIG. 5, so that the outwardly curving portion of the body 110 is oriented to the front side (F) of the body by rotating the artificial disk 100, and the artificial disk is inserted into a stable position. This is a state in which the screw connection is not completely released and facilitates the rotation of the artificial disk 100.

Figure 6:
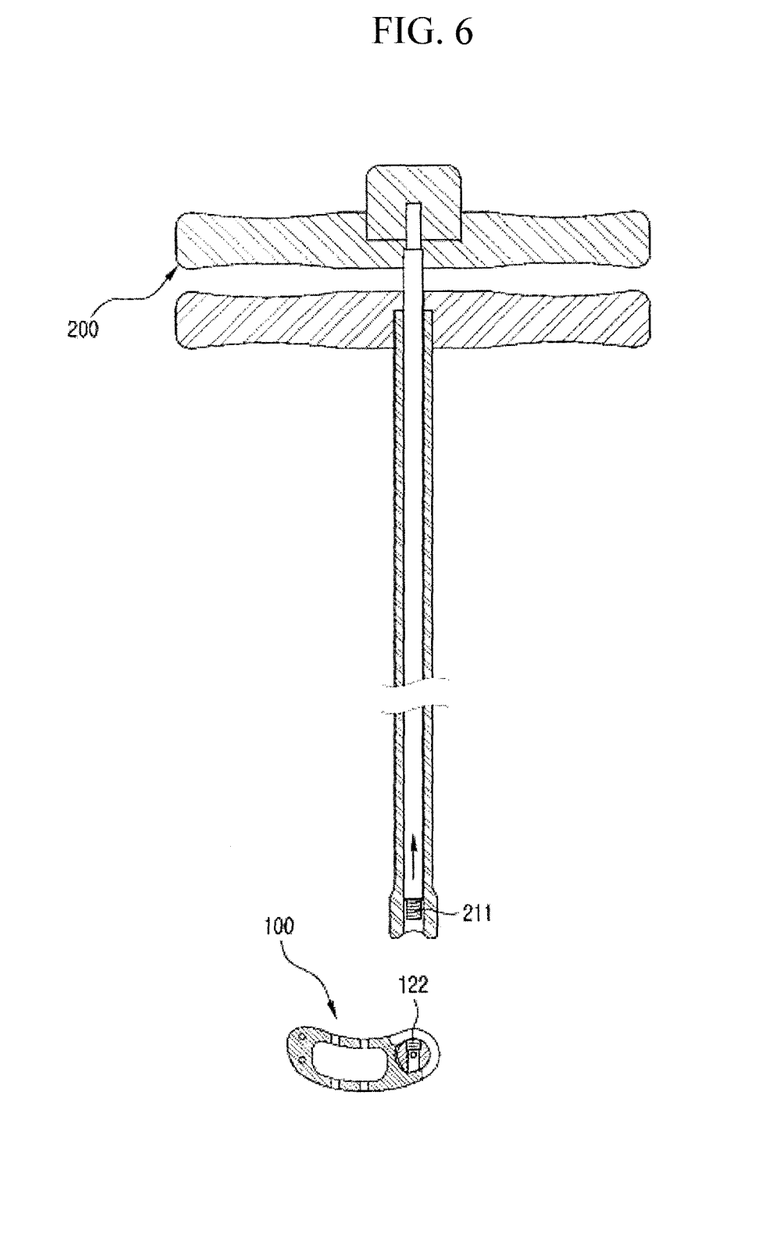

If the artificial disk 100 is completely inserted and placed in the appropriate position and the connecting unit 120 is disconnected from the first insertion tool 200 by unscrewing the first insertion tool 200 as shown in FIG. 6, the insertion of the artificial disk 100 is completed by drawing out the first insertion tool 200 and the second insertion tool 300 altogether.

As described above, the rotation radius of the artificial disk 100 may be controlled by the guide protrusion 121 and the guide recess 113, and also may be controlled by the incision recess 111 and the insertion end 312 of the second insertion tool 300. Accordingly, the rotation radius may be appropriately realized according to a design. In this embodiment, a rotation of 90° is illustrated, but a rotation may be realized by a lower degree.

While the invention has been shown and described with reference to certain exemplary thereof, it will be understood by those skilled in the art that various changes in form and details may be made therein without departing from the spirit and scope of the invention as defined by the appended claims and their equivalents.

What is claimed is:

1. An assembly for inserting an artificial disk, the assembly comprising: an artificial disk which comprises:
   a body which has a predetermined thickness to be inserted between vertebrae, and comprises an incision recess incised on one side of the body in a sideways direction and a penetrating hole formed on the side on which the incision recess is formed in a vertical thickness direction that is perpendicular to the sideways direction, and a connecting unit which is inserted into the penetrating hole and serves as a shaft of a rotational movement of the body, and comprises a connecting hole formed on a side surface of the connecting unit, and a guide protrusion to be inserted into a guide recess formed on a part of the body that is not incised;
   a first insertion tool which comprises a connecting rod which has a predetermined length and has a connecting protrusion formed on one end thereof in a stepwise shape to be inserted into the connecting hole, and a handle which is formed on the other end for manipulating and rotating of the artificial disk; and
   a second insertion tool which comprises a support rod which has a predetermined length and has a hollow through which the connecting rod of the first insertion tool penetrates, and which comprises an insertion end which is formed on one end of the support rod to be inserted into the incision recess and is rounded in a shape corresponding to an appearance of the connecting unit, and a support end which projects from the insertion end in a stepwise shape and is rounded in a shape corresponding to an appearance of the side of the body on which the incision recess is formed, and a handle which is formed on the other end.

2. The assembly as claimed in claim 1, where the support end of the support rod is rounded in the shape corresponding to the appearance of the side of the body on which the incision recess is formed, so that a rotational movement of the body is limited to a maximum rotation radius between opposite ends of the incision recess formed along an outer circumference of the body, and the incision recess has an incision length of one side longer than that of the other side with reference to a lengthwise direction of the connecting rod.

3. The assembly as claimed in claim 2, wherein the incision length of the one side of the incision recess limits the rotational movement of the body within 90°.

4. The assembly as claimed in claim 1, wherein the rotational movement of the body, which is rotated about the connecting unit, is limited by the guide protrusion of the connecting unit corresponding to the guide recess.

5. The assembly as claimed in claim 4, wherein a length of the guide recess limits the rotational movement of the body within 90°.

6. The assembly as claimed in claim 1, wherein the artificial disk further comprises:
   a first fixing part which covers one side of the penetrating hole and has a diameter larger than that of the penetrating hole, and which is inserted into an uneven portion formed on the body and has a shaft rod to be inserted into a shaft hole formed in the connecting unit; and
   a second fixing part which covers the other side of the penetrating hole and has a diameter larger than that of the penetrating hole, and which is inserted into an uneven portion formed on the body and has a shaft rod connecting hole into which the shaft rod of the first fixing part is inserted.

7. The assembly as claimed in claim 1, wherein if the connecting protrusion of the first insertion tool is tightly screwed into the connecting hole of the connecting unit, the connecting unit is brought into close contact with the insertion end and the support end of the second insertion tool and the body is brought into close contact with the support end, so that the body is not rotated unless an external force greater than a predetermined force is applied.

* * * * *